United States Patent
Khalaj

(10) Patent No.: US 9,227,047 B2
(45) Date of Patent: Jan. 5, 2016

(54) CATHETER CONNECTOR

(71) Applicant: Kimberly-Clark Worldwide, Inc., Neenah, WI (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 14/066,045

(22) Filed: Oct. 29, 2013

(65) Prior Publication Data
US 2015/0119855 A1    Apr. 30, 2015

(51) Int. Cl.
*A61M 39/10*    (2006.01)
*A61M 5/34*     (2006.01)
*A61M 39/06*    (2006.01)
*A61M 39/12*    (2006.01)

(52) U.S. Cl.
CPC ........... *A61M 39/10* (2013.01); *A61M 5/344* (2013.01); *A61M 5/346* (2013.01); *A61M 39/06* (2013.01); *A61M 39/1011* (2013.01); *A61M 39/12* (2013.01); *A61M 2039/062* (2013.01); *A61M 2039/066* (2013.01); *A61M 2039/1033* (2013.01)

(58) Field of Classification Search
CPC ............... A61M 39/16; A61M 39/26; A61M 2039/062; A61M 2039/066; A61M 2039/1033; A61M 39/06; A61M 39/10; A61M 39/1011; A61M 39/12; A61M 5/344; A61M 5/346; F16L 37/38
See application file for complete search history.

(56) References Cited

U.S. PATENT DOCUMENTS

| | | | |
|---|---|---|---|
| 4,842,592 A * | 6/1989 | Caggiani et al. | 604/535 |
| 5,464,400 A | 11/1995 | Collins | |
| 6,698,424 B2 | 3/2004 | Madsen et al. | |
| 7,044,936 B2 | 5/2006 | Harding et al. | |
| 7,666,178 B2 | 2/2010 | McMichael | |
| 8,142,418 B2 | 3/2012 | McMichael et al. | |
| 8,205,917 B2 | 6/2012 | Brewer et al. | |
| 8,256,422 B2 | 9/2012 | Brewer et al. | |
| 8,307,829 B2 | 11/2012 | Brewer et al. | |
| 8,449,528 B2 | 5/2013 | Griffith et al. | |
| 2002/0032436 A1 * | 3/2002 | Mogg | 606/1 |

* cited by examiner

*Primary Examiner* — Imani Hayman
(74) *Attorney, Agent, or Firm* — Dority & Manning, P.A.

(57) ABSTRACT

A catheter connector and method of use is disclosed. The catheter connector includes a body, a proximal end port, and a seal. The body has a proximal end and a distal end. Further, the body defines a hollow interior from the proximal end to the distal end. The hollow interior is configured to receive a catheter at least partially therethrough. The proximal end port includes a cavity and is configured with the proximal end of the body for mating communication with a fluid delivery device, such as a pump, reservoir, syringe, or the like. This port may have any conventional configuration, such as a Luer-lock fitting. The seal is configured within the interior of the body and includes a passage configured for receipt of the catheter. In addition, at least a portion of the seal is configured within the cavity of the proximal end port. Further, the seal is configured to compress around the catheter so as to axially secure the catheter within the body.

19 Claims, 6 Drawing Sheets

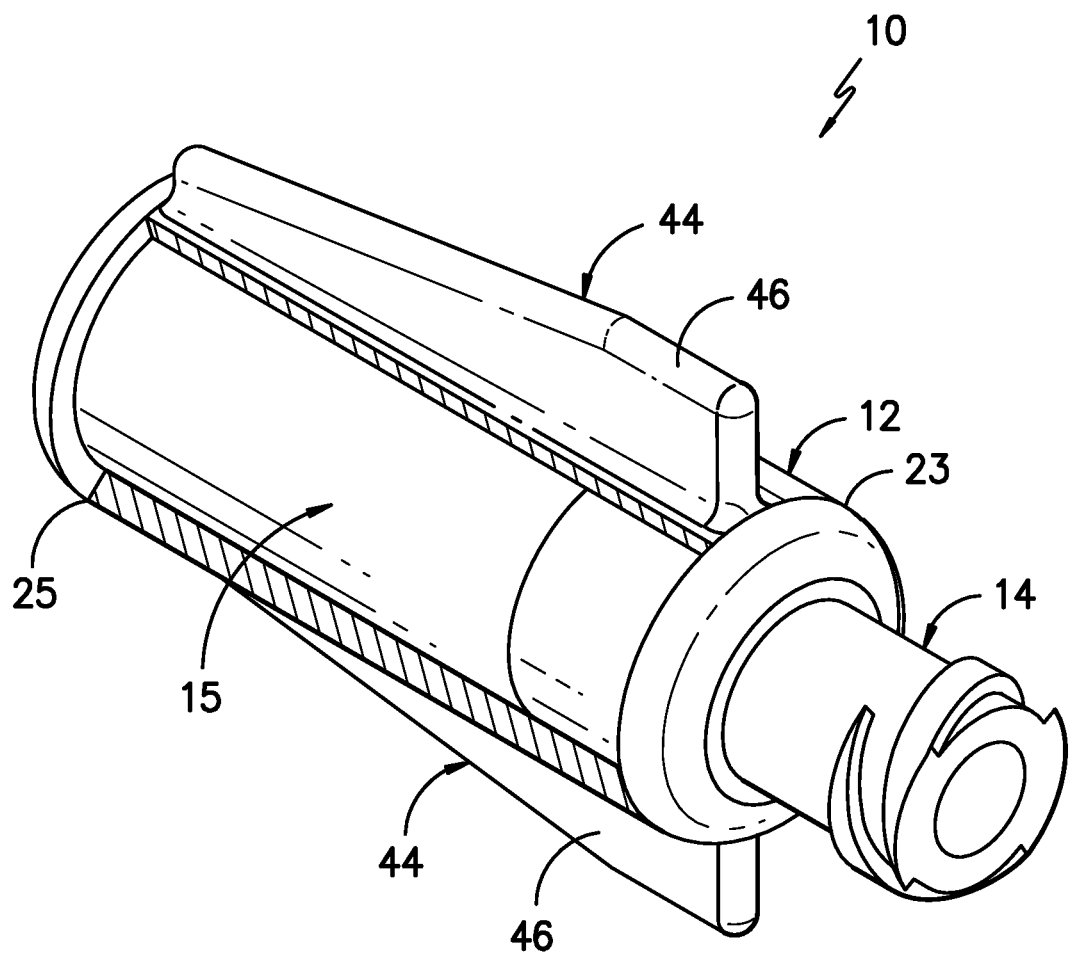
FIG. -1-

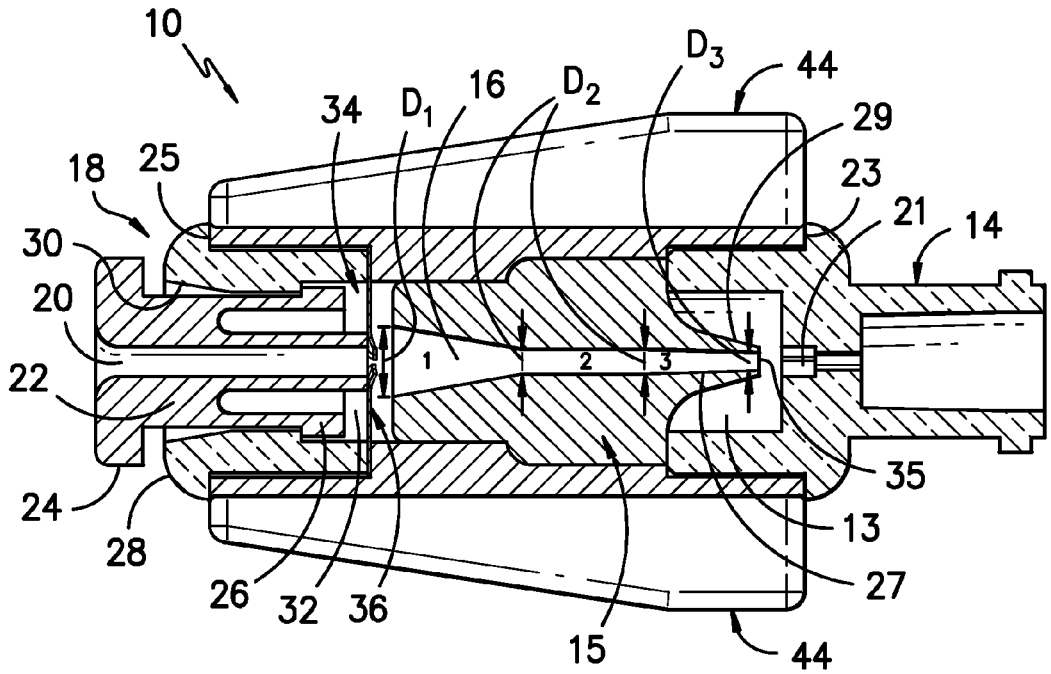
FIG. -2-
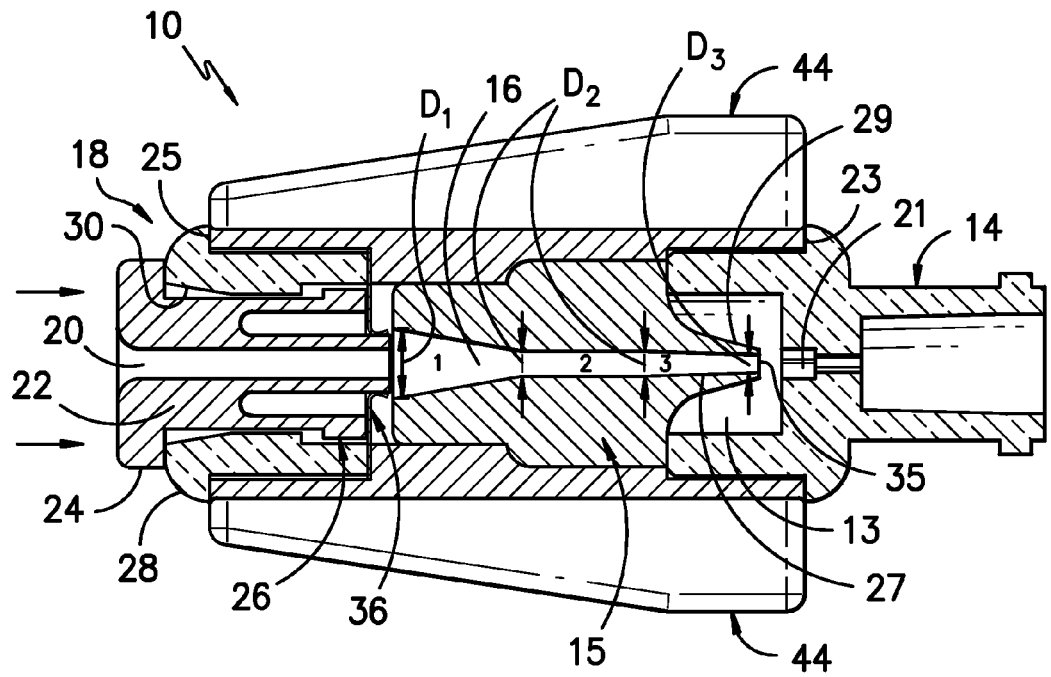
FIG. -3-

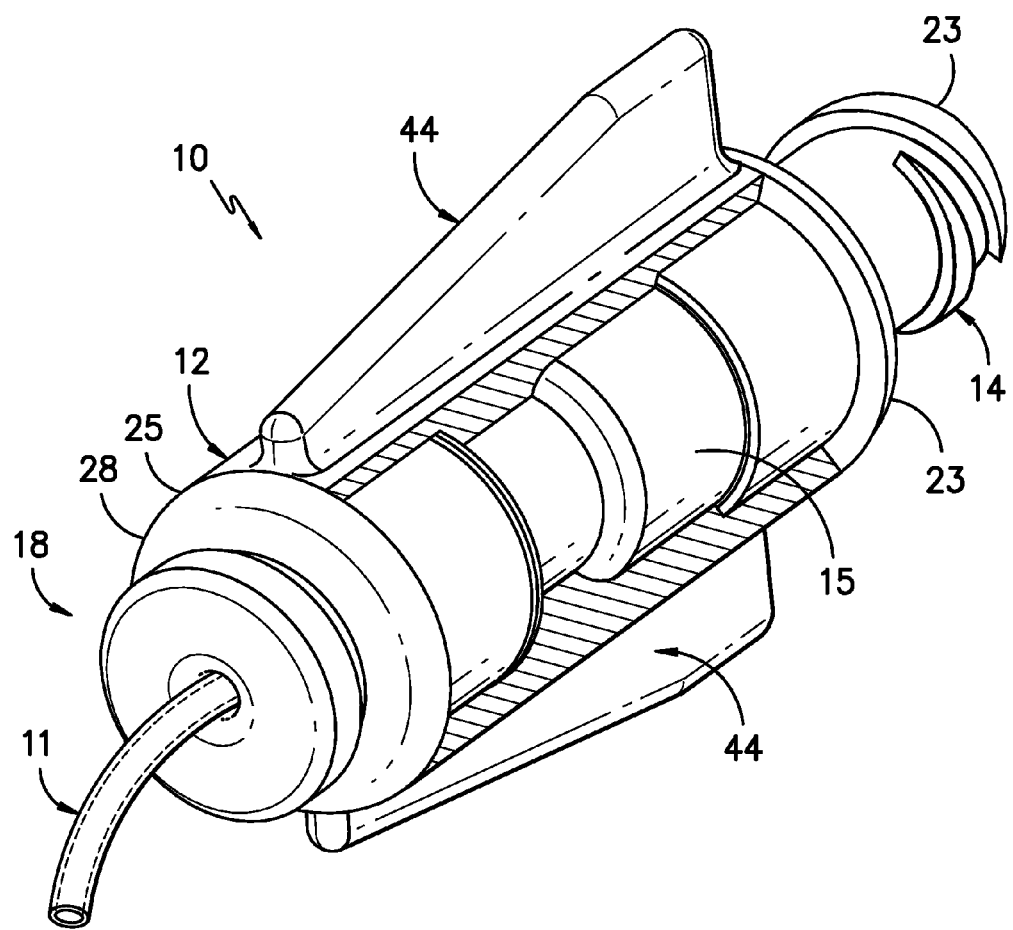
FIG. —4—

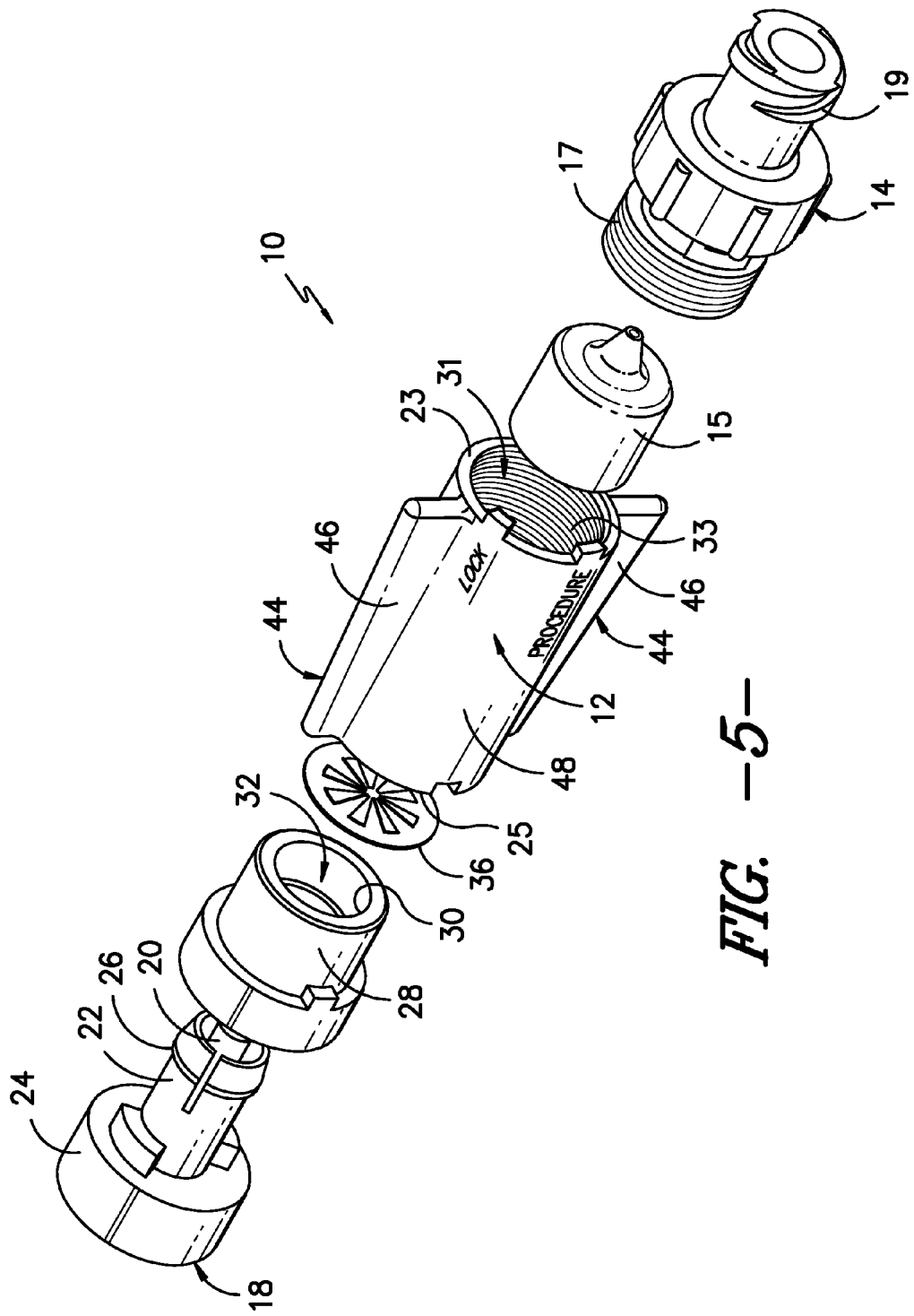
FIG. -5-

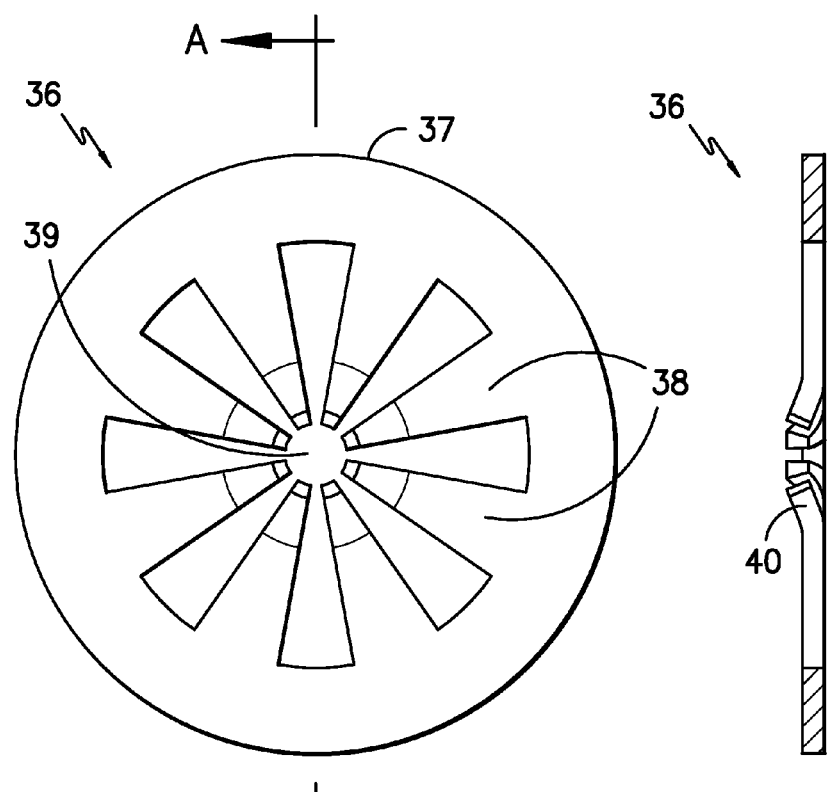
FIG. -6-
FIG. -7-

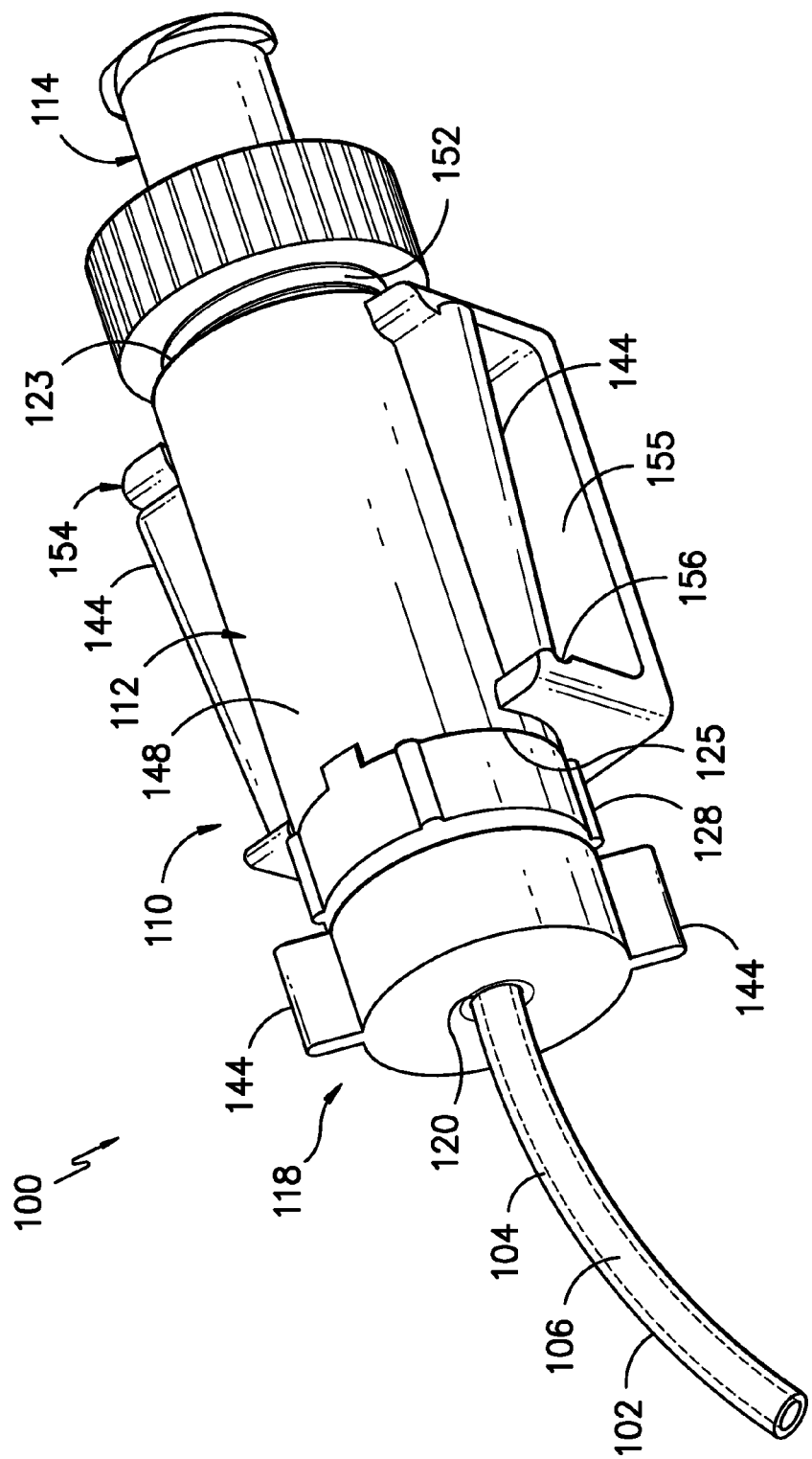
FIG. -8-

CATHETER CONNECTOR

FIELD OF THE INVENTION

The present invention relates generally to the field of medical catheters, and more particularly to catheter connectors.

BACKGROUND

The use of catheters to deliver or withdraw fluids from a patient for various medical procedures is well known. For example, U.S. Pat. No. 7,959,623 describes a pain management system that uses various embodiments of infusion catheters to deliver fluid medication from a pump, through tubing, to a wound site. With such configurations, catheter connectors are typically used to connect the catheter to various devices, such as tubing, a fluid reservoir or other fluid delivery device, and so forth. In the system of the '623 patent, a conventional Toughy Borst connector is used to connect the distal end of a medical tube to the proximal end of the catheter.

In addition to Tuohy-Borst connectors, various other configurations of catheter connectors are available. For example, Epimed International of Farmers Branch, Tex., USA, manufactures a low profile twist-lock catheter connector known as the "Stingray™ Connector." This device has axially aligned halves that twist to an open position to allow insertion of the catheter in a first half, and subsequently twist to a closed position with and audible and tactile click that indicates complete engagement with the catheter. The second half connects to a tube or other fluid delivery device for delivering fluid through the connector to the catheter.

Smiths Medical International Ltd. of the United Kingdom offers a catheter connector under the "EpiFuse™" trade name that consists of two halves joined by a living hinge. A catheter is inserted into a hole at the base of the connector and is retained when the two halves are folded and locked together.

Coupling of the catheter connector to the catheter needs to be quick and easy, as there is little to no time for a doctor or nurse to adjust and/or study the device. As such, the medical art is continuously seeking new and improved catheter connectors that provide quick and reliable connection. The present invention provides such a connector.

SUMMARY OF THE INVENTION

Objects and advantages of the invention will be set forth in part in the following description, or may be obvious from the description, or may be learned through practice of the invention.

In certain aspects, the present invention relates to a catheter connector. The catheter connector includes a body, a proximal end port, and a seal. The body has a proximal end and a distal end. Further, the body defines a hollow interior from the proximal end to the distal end. The hollow interior is configured to receive a catheter at least partially therethrough. The proximal end port includes a cavity and is configured with the proximal end of the body for mating communication with a fluid delivery device, such as a pump, reservoir, syringe, or the like. This port may have any conventional configuration, such as a Luer-lock fitting. The seal is configured within the interior of the body and includes a passage configured for receipt of the catheter. In addition, at least a portion of the seal is configured within the cavity of the proximal end port. Further, the seal is configured to compress around the catheter so as to axially secure the catheter within the body.

In a further embodiment, the seal may include a tapered inner surface, a tapered outer surface, or a combination thereof. More specifically, at least a portion of the passage of the seal may include a tapered inner surface. Further, the seal may further include a tapered outer surface, wherein the portion of the seal configured within the cavity includes the tapered outer surface. In another embodiment, the proximal end port may include a recess configured to receive a proximal end of the catheter. As such, the recess provides a hard stop for the catheter when inserted within the catheter connector. Further, the recess may be in fluid communication with the cavity.

In certain embodiments, the proximal end port may include a threaded outer surface corresponding to a threaded inner surface of the body. As such, the threaded outer surface is configured for mating communication with the threaded inner surface of the body. Further, when the threaded outer surface of the proximal end port is engaged with the threaded inner surface of the body, the proximal end port is configured to compress the seal such that the seal compresses around the catheter so as to axially secure the catheter within the body.

In still additional embodiments, the catheter connector includes an axially-extending push component having a shaft and a housing. The shaft includes a bore defined therethrough configured for receipt of the catheter. The housing is configured with the distal end of the body and comprises an interior wall defining an opening. The opening is configured for receipt of the shaft such that the interior wall circumferentially engages around the shaft. Further, the shaft is configured to move axially between an open position and a locked position.

In further embodiments, the shaft may include a push cap configured to abut against the housing when the push component is in the open position. In still another embodiment, the shaft may include a radial lip that corresponds to a groove of the interior wall of the housing. In a further embodiment, the radial lip may be a continuous, circumferential member that continuously engages around and against the shaft. Similarly, the groove may be a continuous, circumferential groove configured for receipt of the continuous radial lip. Further, the radial lip may be configured to move within the groove when the push component moves between the open and locked positions.

In still further embodiments, the catheter connector may include a plate configured within the body. For example, in one embodiment, the plate may be configured between a proximal end of the shaft of the push component and a distal end of the seal. As such, when the push component is in the open position, the shaft is configured to engage the plate such that the catheter can be freely inserted or released from the catheter connector. When the push component is in the locked position, the plate is configured to axially lock the catheter within the body. More specifically, the plate may include a plurality of spokes extending radially to a center opening. As such, in the open position, the shaft pushes through the center opening such that the plurality of spokes are pushed towards the proximal end of the body, thereby allowing the catheter to be freely inserted or released from the catheter connector. Further, in the locked position, the plurality of spokes are configured to engage and axially lock the catheter within the body. It should be understood that the plurality of spokes may be any suitable shape such as a triangular, rectangular, arcuate, or similar shape. In a further embodiment, each of the plurality of spokes may include a slanted end. As such, each of the slanted ends may be biased towards the proximal end of the body such that the shaft may be easily inserted therethrough.

In certain embodiments, the catheter connector may further include one or more flanges configured on an outer surface of the body. The flanges are configured to assist a user with gripping and/or rotating the catheter connector. In still another embodiment, the catheter connector may include one or more visual indicators on the outer surface of the body configured to assist a user in operating the catheter connector.

In another aspect, a method of using a catheter connector is disclosed. The catheter connector is of the type having a seal configured therein. The method includes: inserting a needle and a distal end of a catheter into a patient; inserting a proximal end of the catheter into a distal end of the catheter connector and through at least a portion of the seal; injecting a fluid into a cavity of a proximal end port configured with a proximal end of the catheter connector, wherein at least a portion of the seal is configured within the cavity; and securing a portion of the catheter via the seal compressing around the catheter.

In certain embodiments, the step of injecting the fluid into the cavity of the proximal end port provides a fluid pressure that creates a hermetic seal between the seal and the catheter. In a further embodiment, the method further includes axially pushing a push component configured with the distal end of the catheter connector to an open position, inserting the proximal end of the catheter through a bore of the push component, and moving the push component to a locked position. Further, the method may include inserting the proximal end of the catheter through a plate configured with the push component, wherein the plate is configured to temporarily lock the catheter within the catheter connector when the push component is in a locked position. The plate of the catheter connector may further includes a plurality of spokes extending radially to a center opening. As such, the method may further include inserting the proximal end of the catheter through the center opening such that the plurality of spokes engage and lock the catheter within the catheter connector when the push component is in a locked position.

In a further embodiment, the method may further include removing the needle from the patient, axially pushing the push component to the open position, releasing the catheter from the catheter connector, and removing the needle from over the catheter. In addition, the method may include axially re-pushing the push component to the open position, reinserting the catheter into the catheter connector such that at least a portion of the catheter is inserted within the seal, and securing the proximal end port within the proximal end of the catheter connector so as to compress the seal via moving the positions of the seal and the proximal end port closer together. In a particular embodiment, the step of securing the proximal end port within the proximal end of the catheter connector so as to compress the seal further includes screwing a threaded outer surface of the proximal end port into a threaded inner surface of the body of the catheter connector such that the seal compresses around the catheter so as to axially secure the catheter within the body.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

FIG. 1 is a perspective view of one embodiment of a catheter connector in accordance with aspects of the invention;

FIG. 2 is a cross-sectional view of one embodiment of a catheter connector in an open position in accordance with aspects of the invention;

FIG. 3 is a cross-sectional view of one embodiment of a catheter connector in a locked position in accordance with aspects of the invention;

FIG. 4 is a perspective view of another embodiment of the catheter connector connected to a catheter in accordance with aspects of the invention;

FIG. 5 is an exploded perspective view of another embodiment of a catheter connector in accordance with aspects of the invention;

FIG. 6 is a top view of one embodiment of a plate in accordance with aspects of the invention;

FIG. 7 is a cross-sectional view of the embodiment of FIG. 6 along line A-A in accordance with aspects of the invention; and FIG. 8 is a perspective view of another embodiment of a catheter connector in accordance with aspects of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

Referring now to the drawings, FIGS. 1-5 illustrate various views of one embodiment of the catheter connector 10 according to the present disclosure. As shown, the catheter connector 10 includes a body 12 having a proximal end 23 and distal end 25. The proximal end 23 includes a proximal end port 14 configured thereon for mating communication with a fluid delivery device (not shown). The fluid delivery device may be any suitable device known in the art, such as a pump, reservoir, syringe, or the like. Further, the proximal end port 14 may have any conventional configuration, such as a Luer-lock fitting. For example, as shown, the proximal end port 14 includes fitting 19 to assist in mating the connector 10 to the fluid delivery device. In a further embodiment, the proximal end port 14 further includes a cavity 13 and a recess 21. The recess 21 is in fluid communication with the cavity 13 and is configured to receive a proximal end of the catheter 11. In one embodiment, the recess 21 includes a first dimension and a second dimension. As such, the recess 21 may define a hard stop for the catheter 11 between the first and second dimensions such that the catheter 11 can only be inserted into the connector 10 up to the second dimension. Such a hard stop can signal to a user than the catheter 11 is in a proper position.

Referring particular to FIGS. 2, 3, and 5, the catheter connector 10 also includes a seal 15 capable of providing multiple sealing capabilities within the catheter connector 10. As shown, the seal 15 is configured within the interior 31 of the body 12. Further, the seal 15 includes a passage 16 configured for receipt of the catheter 11. Moreover, the passage 16 of the seal 15 is configured to axially align with the proximal end port 14. As shown in FIGS. 2 and 3, at least a portion of the seal 15 is configured within the cavity 13 of the proximal end port 14. As such, in one embodiment, when fluid is delivered into the cavity 13, fluid pressure builds up in the cavity 13 such that the seal 15 deforms around the catheter 11 within the connector 10. More specifically, in another embodiment, the fluid pressure is capable of providing a hermetic or airtight seal around the catheter 11. In another embodiment, the proximal end port 14 may include a threaded outer surface 17 that corresponds to a threaded inner surface 33 of the body 12. As such, when the threaded outer surface 17 of the proximal end port 14 engages the threaded inner surface 33 of the body 12, the proximal end port 14 is configured to compress the seal 15 such that the seal 15 compresses around and seals the catheter 11, thereby axially securing the catheter 11 within the body 12.

In still additional embodiments, the passage 16 may have one or more sections having varying diameters and/or tapered inner surfaces 27. As an example, the passage 16, as shown in the embodiment of FIGS. 2 and 3, has three sections. In the first illustrated section, labeled 1, the passage 16 tapers from a first diameter $D_1$ to a second diameter $D_2$. The first diameter $D_1$ is larger than a diameter of the catheter 11, whereas the second diameter $D_2$ is less than the first diameter $D_1$, but still larger than a diameter of the catheter 11. As such, the catheter 11 may be easily inserted into the first diameter $D_1$ of the passage 16 and guided through the seal 15 to the second diameter $D_2$. The second section of the passage 16, labeled 2, is a straight section (i.e. it does not taper) such the diameter of the entire cross-section is equal to the second diameter $D_2$. The third section, labeled 3, tapers from the second diameter $D_2$ to a third diameter $D_3$, wherein the third diameter $D_3$ is the closest dimension to the catheter diameter. In addition, as shown in the embodiment of FIGS. 2 and 3, the outer surface 29 of the seal 15 (adjacent to the third section 3) may also taper. As such, the blunt surface or sharp edge 35 created by the tapered surfaces 27, 29 at the proximal end of the seal 15 creates a more efficient seal around the catheter 11 when fluid enters the cavity 13 of the proximal end port 14. In further embodiments, the passage 16 may have more or less than three sections. For all embodiments, the varying diameters of the passage 16 transition from larger than the outside diameter of catheter 11 on the distal side of the seal 15 to closer to the actual dimension of the outside diameter of the catheter 11 on the proximal side of seal 15.

In a further embodiment, the catheter connector 10 may also include an axially-extending push component 18 configured at the distal end 25 of the body 12. In another embodiment, the push component 18 is a separate feature connected at the distal end 25 of the body 12. Alternatively, the push component 18 may be integral with the body 12. The push component 18 is configured to move axially between an open position (FIG. 2) and a locked position (FIG. 3). Further, the push component 18 includes a shaft 22 and a housing 28. The shaft 22 includes a bore 20 defined therethrough that axially aligns with the port 14 and is sized for sliding receipt of a catheter 11 inserted therein (FIG. 4). The housing 28 is configured to seat within the distal end 25 of the body 12. Further, the housing 28 includes an interior wall 30 defining an opening 32 therethrough. The opening 32 of the housing 28 is configured for receipt of the shaft 22 such that the interior wall 30 of the housing 28 circumferentially engages around the shaft 22. For example, as shown in the illustrated embodiments, the shaft 22 has a generally cylindrical shape and the opening 32 has a corresponding cylindrical shape. It should be understood that the shaft 22 and the housing 28 may have any suitable corresponding shapes known in the art.

In a further embodiment, the push component 18 may also include a push cap 24 configured to abut against the housing 28 when the push component 18 is in the open position. As such, the push cap 24 may limit the range of motion of the shaft 22 relative to the housing 28. In addition, the push component 18 may include a radial lip 26. For example, as shown in the embodiments of FIGS. 2, 3, and 5, the radial lip 26 is located at a proximal end of the push component 18. In further embodiments, the radial lip 26 may be located at any location along the push component 18. In certain embodiments, the radial lip 26 may be a continuous circumferential member that continuously engages around and against a portion of the interior wall 30 of the housing 28.

In addition, the interior wall 30 of the housing 28 may have a groove 34 defined therein corresponding to the radial lip 26 of the shaft 22. In one embodiment, the groove 34 may be a continuous, circumferential groove such that the groove 34 is configured for receipt of the radial lip 26. Further, the radial lip 26 may be configured to move within the recess 34 when the push component 18 moves between the open position (FIG. 3) and the locked position (FIG. 3).

In a further embodiment, the catheter connector 10 may optionally include a plate 36 configured to secure the catheter 11 within the catheter connector 10. The plate 36 may be configured at any suitable location within the body 12 of the connector 10. For example, as shown in the illustrated embodiments, the plate 36 is configured between the bore 20 of the push component 18 and the passage 16 of the seal 15. As such, when the push component 18 is in the open position (FIG. 3), the shaft 22 is configured to engage the plate 36 such that the catheter 11 can be inserted or released from the catheter connection 10. Further, when the push component 18 moves to the locked position (FIG. 2), the plate 36 axially locks the catheter 11 within the body 12.

More specifically, and referring to FIGS. 5-7, the plate 36 may include a plurality of spokes 38 extending radially from an outer circumference 37 towards a center opening 39. As such, when the push component 18 is in the open position (i.e. when a user pushes the push component 18 towards the proximal end 23 of the body 12), the shaft 22 of the push component 18 is configured to push through the center opening 39 of the plate 36. Accordingly, the plurality of spokes 38 are displaced towards the proximal end 23 of the body 12 and the catheter 11 may be inserted through or released from the center opening 39. When the push component 18 moves to the locked position (i.e. a user releases the push component 18), the plurality of spokes are configured to surround and axially lock the catheter 11 within the body 12 of the connector 10.

It should be understood that the plurality of spokes 38 may be any suitable shape such as a triangular, rectangular, arcuate, or similar shape. In additional embodiments, each of the plurality of spokes 38 may have the same shape or may each have a different shape. Further, in one embodiment, each of the plurality of spokes 38 may include a slanted end 40. As such, each of the slanted ends 40 may be biased towards the proximal end 23 of the body 12 such that the shaft 22 may be easily inserted therethrough. Accordingly, the slanted ends 40 of the plate 36 are configured to assist in securing the catheter 11 within the catheter connector 10.

Referring back to FIGS. 1-5, the catheter connector 10 may also include one or more flanges 44 to assist a user with gripping and/or rotating the catheter connector 10. The flanges 44 may be located at any location on an outer surface of the catheter connector 10. For example, as shown, the flanges 44 are configured on an outer surface 48 of the body 12. Alternatively, as shown in FIG. 8, the flanges 144 may be configured on an outer surface 148 of the push component 118. In still further embodiments, the connector may include flanges in multiple locations, as shown in FIG. 8. Further, it should be understood that the flanges 44, 144 may be configured at any location on the catheter connector 10, 110. More specifically, the flanges 44, 144 may be configured on opposite sides of the body 12 or spaced at any suitable configuration about the circumference of the catheter connector 10, 110. As such, the flanges 44, 144 provide a quick and easy grip for a user to assist the user with rotating the catheter connector 10, 110.

In another aspect, a method of using the catheter connector as described herein is disclosed. The method may include steps of using the catheter in a temporary manner, a permanent manner, or a combination of both. Temporary use of the catheter connector typically refers to use relating to quick administering of fluids and/or medicines, such as by a syringe, and generally involves the needle remaining in the patient. Permanent use of the catheter connector typically refers to use relating to long-term administering of fluids and/or medicines, such as by a pump, and generally involves the needle being removed from the patient. As such, the catheter connector 10 may include one or more visual indicators indicating whether the connector 10 is being operated in a temporary or permanent mode. For example, as shown in FIG. 5, the body 12 of the connector 10 includes the terms "LOCK" (corresponding to a permanent mode) and the term "PROCEDURE" (corresponding to a temporary mode). It should be understood in the art that the any suitable terms or indicators may be used to indicate the mode of the connector 10.

In one embodiment including temporary use of the catheter connector 10, a user may first insert a distal end of a needle and catheter assembly into the patient. The user may then insert a proximal end of the catheter into a distal end of the catheter connector until the catheter reaches a hard stop within the connector. In one embodiment, the hard stop is synonymous with the recess 21 of the proximal end port 14. In further embodiments, the catheter 11 can be configured to stop at any location within the catheter connector 10. For example, the catheter 11 may be inserted into at least a portion of the seal 15 a predetermined distance. Once properly inserted, the user axially pushes the push component 18 to the open position such that the shaft 22 of the push component 18 engages the plate 36 and allows the catheter 11 to be inserted therein. The user can then move the push component 18 to the locked position to temporarily lock the catheter 11 within the connector 10. The user can then connect the catheter connector 10 to a fluid delivery device (e.g. a syringe) such that fluid is injected into the cavity 13 of the proximal end port 14. The fluid pressure from injection causes the seal 15 to deform around the catheter 11, thereby sealing the proximal end of the catheter 11 within the catheter connector 10. The combination of the plate 36 locking the catheter 11 and the seal 15 deforming around and sealing the catheter 11 temporarily secures the catheter 11 within the catheter connector 10 such that the user can administer fluids to the patient quickly and effectively, while the needle is still in the patient, if needed.

In a further embodiment, wherein permanent use is desired after temporary use of the catheter connector 10, a user may remove the needle from the patient and over the catheter 11. The user can then either use a hub of the needle or one or more of his fingers to assist in pushing the push component 18 to the open position. As such, the plurality of spokes 38 of the plate 36 are displaced towards the proximal end 23 of the body 12, thereby releasing the catheter 11 from the connector 10. The user is then capable of removing the needle from the catheter 11. After removal of the needle, the user can reconnect the catheter 11 and the connector 10 in a permanent manner. As such, the user again pushes the push component 18 to the open position and inserts the catheter 11 until it again reaches a hard stop, typically corresponding to recess 21. The user can then optionally move the push component 18 to the locked position. To permanently lock the catheter 11 within the catheter connector 10, the user tightens or screws the proximal end port 14 into the proximal end 23 of the body 12 of the catheter connector 10 so as to compress the seal 15. In one embodiment, the connector 10 may include a visual indicator signaling to the user when to stop tightening the proximal end port 14. In another embodiment, the user may tighten the proximal end port 14 until he cannot tighten further. As such, the proximal end port 14 compresses the seal 15 around the catheter 11, which creates a more secure connection than the fluid pressure and plate configuration described above in regards to the temporary securement. To release the catheter 11 from the connector 10 in a permanent mode, the user can simply unscrew or loosen the proximal end port 14 such that the seal 15 is no longer compressed. As such, the catheter 11 can be easily removed.

In another embodiment, temporary securement of the catheter 11 may not be needed, in which case the user can simply neglect the steps above in regards to temporary use. In this case, the user first inserts the distal end of the needle and catheter assembly into the patient. The user then removes the needle from the patient and over the catheter. The user then inserts the catheter 11 into the interior 31 of the body 12 and at least partially within the seal 15. The user may then tighten or screw the proximal end port 14 into the proximal end 23 of the body 12 of the catheter connector 10 so as to compress the seal 15 around the catheter 11. It should be understood that this embodiment may or may not include the push component 18 and plate 36 configuration as described herein, for example, as shown in FIG. 1.

Referring now to FIG. 8, the catheter connection may be a part of a larger connector assembly 100 for use with a catheter 102. As shown, the connector assembly 100 includes a catheter 102 having a proximal end (secured within the catheter connector 110), a distal end (not shown), and walls 104 defining a lumen 106. As previously discussed, the catheter connector 110 includes a body 112 having a proximal end 123 and distal end 125. The proximal end 123 includes a proximal end port 114 configured thereon for mating communication with a fluid delivery device (not shown). It should be understood that the catheter connector 110 may include any of the features described herein. For example, the catheter connector 100 may further include a seal configured within the body 112 (not shown), a push component 118 configured to move between an open position and a locked position, a housing 128, and a plate (not shown).

In addition, the connector assembly 100 may include a securement device 154 for securing the catheter 102 and the catheter connector 110 relative to a patient. It should be understood that the securement device 154 may be any suitable device known in the art. For example, the securement device 154 may include a base 155 configured to attach to a patient or other suitable surface. Further, the securement device 154 may include one or more grooves for securing the flanges 144. Further, the securement device 154 may include the "Grip-Lok™" securement device from Zefon International Inc. of Ocala, Fla., USA. This device includes an adhesive base layer that attaches to the patient's skin. The catheter/connector assembly is pressed onto an adhesive pad attached to an upper surface of the base layer. A Velcro™ closure layer is then folded over the catheter and attaches to the upper surface of the base layer. Another suitable securement device 154 is disclosed in U.S. Pat. No. 7,635,355 which describes a securement device having an anchor pad that attaches to the patient's skin, with a retainer configured thereon. It should be understood that the previous securement devices are provided by way of example only, and that any suitable securement device could be configured with the catheter connector described herein.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A catheter connector, comprising:
    a body having a proximal end and a distal end, said body defining a hollow interior from said proximal end to said distal end, said hollow interior configured to receive a catheter at least partially therethrough;
    a proximal end port attached to said proximal end of body for mating communication with a fluid delivery device, said proximal end port comprising a cavity;
    a seal positioned within said interior of said body, said seal comprising a passage configured to receive the catheter, wherein at least a portion of said seal is positioned within said cavity of the proximal end port, and wherein a plurality of portions of said passage of said seal are configured to deform around the catheter so as to axially secure the catheter within the body; and
    an axially-extending push component positioned at least partially within said distal end of said body, said push component comprising a shaft and a housing, said shaft comprising a bore defined therethrough configured to receive the catheter, said housing comprising an interior wall defining an opening, said opening configured to receive said shaft such that said interior wall circumferentially engages around said shaft, wherein said shaft is configured to move axially between an open position and a locked position.

2. The catheter connector of claim 1, wherein at least a portion of the passage of the seal comprises a tapered inner surface.

3. The catheter connector of claim 2, wherein the seal further comprises a tapered outer surface, wherein the portion of said seal positioned within said cavity includes said tapered outer surface.

4. The catheter connector of claim 2, wherein said proximal end port further comprises a recess configured to receive a proximal end of the catheter, said recess in fluid communication with said cavity.

5. The catheter connector of claim 1, wherein said proximal end port further comprises a threaded outer surface corresponding to a threaded inner surface of said body, wherein said threaded outer surface of said proximal end port is configured to mate with said threaded inner surface of said body, wherein when engaged with said body, said proximal end port is configured to compress said seal such that seal compresses around and seals the catheter so as to axially secure the catheter within the body.

6. The catheter connector of claim 1, wherein said shaft further comprises a push cap configured to abut against said housing when said push component is in the open position.

7. The catheter connector of claim 1, wherein said shaft comprises a radial lip and said interior wall of said housing comprises a corresponding groove defined therein, said groove configured to receive of said radial lip, said radial lip configured to move within said groove when said push component moves between said open position and said locked position.

8. The catheter connector of claim 1, further comprising a plate positioned at a proximal end of said shaft of said push component, wherein in the open position, said shaft engages said plate such that the catheter can be freely inserted or released from the catheter connector, and wherein in the locked position, said plate axially locks the catheter within said body.

9. The catheter connector of claim 8, wherein said plate further comprises a plurality of spokes extending radially to a center opening, wherein in the open position, said shaft pushes through said center opening such that said plurality of spokes are pushed toward said proximal end of said body thereby allowing the catheter to be freely inserted or released from the catheter connector, and wherein in the locked position, said plurality of spokes engage and axially lock the catheter within said body.

10. The catheter connector of claim 1, further comprising one or more flanges positioned on an outer surface of said body, said flanges configured to assist a user with gripping said catheter connector.

11. The catheter connector of claim 1, wherein said body further comprises one or more visual indicators configured to assist a user in operating the catheter connector.

12. A method of using a catheter connector, the catheter connector comprising: a body having a proximal end and a distal end, said body defining a hollow interior from said proximal end to said distal end, said hollow interior configured to receive a catheter at least partially therethrough; a proximal end port attached to said proximal end of body for mating communication with a fluid delivery device, said proximal end port comprising a cavity; a seal positioned within said interior of said body, said seal comprising a passage configured to receive the catheter, wherein at least a portion of said seal is positioned within said cavity of the proximal end port, and wherein a plurality of portions of said passage of said seal are configured to deform around the catheter so as to axially secure the catheter within the body; and an axially-extending push component positioned at least partially within said distal end of said body, said push component comprising a shaft and a housing, said shaft comprising a bore therethrough configured to receive the catheter, said housing comprising an interior wall defining an opening, said opening configured to receive said shaft such that said interior wall circumferentially engages around said shaft, the method comprising inserting a needle and a distal end of the catheter into a patient; inserting a proximal end of the catheter into a distal end of the catheter connector and through at least the portion of the seal; injecting a fluid into the cavity of the proximal end port configured with a proximal end of the catheter connector, wherein at least the portion of the seal is configured within the cavity; and securing a portion of the catheter within the catheter connector via the seal compressing around the portion of the catheter.

13. The method of claim 12, wherein injecting the fluid into the cavity of the proximal end port provides a fluid pressure that creates a hermetic seal between the seal and the catheter.

14. The method of claim 12, further comprising axially pushing the push component of the catheter connector to an open position, inserting the proximal end of the catheter through the bore of the push component attached to the distal end of the catheter connector, and moving the push component to a locked position.

15. The method of claim 14, further comprising inserting the proximal end of the catheter through a plate positioned on the push component, wherein the plate is configured to temporarily lock the catheter within the catheter connector when the push component is in a locked position.

16. The method of claim 15, wherein said plate further comprises a plurality of spokes extending radially to a center opening, wherein the method further comprises inserting the proximal end of the catheter through the center opening such that the plurality of spokes lock the catheter within the catheter connector when the push component is in the locked position.

17. The method of claim 14, further comprising removing the needle from the patient, axially pushing the push component to the open position, releasing the catheter from the catheter connector, and removing the needle from over the catheter.

18. The method of claim 17, further comprising axially re-pushing the push component of the catheter connector to the open position, reinserting the catheter into the catheter connector such that at least the portion of the catheter is inserted within the seal, and securing the proximal end port within the proximal end of the catheter connector so as to compress the seal.

19. The method of claim 18, wherein securing the proximal end port within the proximal end of the catheter connector so as to compress the seal further comprises screwing a threaded outer surface of the proximal end port into a threaded inner surface of the body of the catheter connector such that the seal compresses around the catheter so as to axially secure the catheter within the body.

\* \* \* \* \*